(12) United States Patent
Song et al.

(10) Patent No.: US 7,057,062 B2
(45) Date of Patent: Jun. 6, 2006

(54) PROCESS FOR MANUFACTURING PURIFIED PHOSPHORODIAMIDITE

(75) Inventors: Quanlai Song, Encinitas, CA (US); Bruce Ross, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 234 days.

(21) Appl. No.: 10/120,680

(22) Filed: Apr. 11, 2002

(65) Prior Publication Data
US 2003/0225284 A1    Dec. 4, 2003

(51) Int. Cl.
C07F 9/02    (2006.01)
(52) U.S. Cl. ..................................... 558/386
(58) Field of Classification Search ................ 558/386
See application file for complete search history.

(56) References Cited

U.S. PATENT DOCUMENTS

| | | | |
|---|---|---|---|
| 4,458,066 A | 7/1984 | Caruthers et al. | 536/27 |
| 4,500,707 A | 2/1985 | Caruthers et al. | 536/27 |
| 4,973,679 A | 11/1990 | Caruthers et al. | 536/27 |
| RE34,069 E | 9/1992 | Köster et al. | 536/27 |
| 5,210,264 A | 5/1993 | Yau | 558/167 |
| 5,783,690 A | 7/1998 | Cheruvallath et al. | 536/55.3 |
| 5,863,905 A * | 1/1999 | Suhadolnik et al. | 514/44 |
| 6,043,353 A | 3/2000 | Pon et al. | 536/25.3 |
| 6,051,699 A | 4/2000 | Ravikumar et al. | 536/25.3 |
| 6,121,437 A | 9/2000 | Guzaev et al. | 536/26.1 |
| 6,124,450 A | 9/2000 | Ravikumar et al. | 536/25.34 |
| 6,160,152 A | 12/2000 | Capaldi | 558/70 |
| 6,169,177 B1 | 1/2001 | Manoharan | 536/25.31 |
| 6,326,478 B1 | 12/2001 | Cheruvallath et al. | 536/23.1 |

OTHER PUBLICATIONS

Cheronis, Nicholas., Semimicro Experimental Organic Chemistry, A Laboratory Manual, J. de Graff, New York, 1958.*
Beaucage, in "Methods in Molecular Biology: Protocols for Oligonucleotides and Analogs," Agrawal, (Ed.), *Humana Press, Totowa*, 1993, 20, 33-61.
Copy of the PCT International Search Report dated Oct. 20, 2003 (PCT/US03/11016).
Castro, B., et al., "Relations reactivite-structure dans les cinetiques de decomposition de sels d'atdp substitutes. Hypersensibilite a des substituants en position 3 de la substitution nucleophile $SN_2$," *Tetrahedron*, 1979, 35(5), 627-632 (English abstract).

* cited by examiner

*Primary Examiner*—Kamal A. Saeed
*Assistant Examiner*—Rebecca Anderson
(74) *Attorney, Agent, or Firm*—ISIS Patent Department

(57) ABSTRACT

A scalable process for purification of phosphorodiamidite includes steps of solubilizing a crude phosphorodiamidite in an apolar organic solvent, contacting the non-polar organic solvent with a polar phase comprising a polar organic solvent to remove impurities from the solubilized phosphorodiamidite, and removing the non-polar organic solvent from the phosphorodiamidite.

34 Claims, No Drawings

PROCESS FOR MANUFACTURING PURIFIED PHOSPHORODIAMIDITE

FIELD OF THE INVENTION

The present invention relates to processes for manufacturing phosphorodiamidites having improved purity. The present invention further provides processes using such purified phosphorodiamidites.

BACKGROUND OF THE INVENTION

It is well known that most of the bodily states in mammals, including most disease states, are effected by proteins. Such proteins, either acting directly or through their enzymatic functions, contribute in major proportion to many diseases in animals and man. Classical therapeutic methods have generally focused on interactions with such proteins in efforts to moderate their disease-causing or disease-potentiating functions. Recently, however, attempts have been made to moderate the actual production of such proteins by interactions with molecules that direct their synthesis, such as intracellular RNA. By interfering with the production of proteins, it has been hoped to effect therapeutic results with maximal desired effect and minimal side effects. It is the general object of such therapeutic approaches to interfere with, or otherwise modulate, gene expression leading to undesired protein formation.

One method for inhibiting specific gene expression is the use of oligonucleotides and oligonucleotide analogs as "antisense" agents. The oligonucleotides or oligonucleotide analogs complimentary to a specific, target, messenger RNA (mRNA) sequence are used. Antisense methodology is often directed to the complementary hybridization of relatively short oligonucleotides and oligonucleotide analogs to single-stranded mRNA or single-stranded DNA such that the normal, essential functions of these intracellular nucleic acids are disrupted. Hybridization is the sequence specific hydrogen bonding of oligonucleotides or oligonucleotide analogs to Watson-Crick base pairs of RNA or single-stranded DNA. Such base pairs are said to be complementary to one another.

Oligonucleotides and oligonucleotide analogs are now accepted as therapeutic agents holding great promise for therapeutic and diagnostic methods. Application of oligonucleotides and oligonucleotide analogs as antisense agents for therapeutic purposes and diagnostic purposes, and as research reagents, often requires that the oligonucleotides or oligonucleotide analogs be synthesized in large quantities.

Three principal methods have been used for the synthesis of oligonucleotides. The phosphotriester method, as described by Reese, *Tetrahedron* 1978, 34, 3143; the phosphoramidite method, as described by Beaucage, in *Methods in Molecular Biology: Protocols for Oligonucleotides and Analogs*; Agrawal, ed.; Humana Press: Totowa, 1993, Vol. 20, 33–61; and the H-phosphonate method, as described by Froehler in *Methods in Molecular Biology: Protocols for Oligonucleotides and Analogs* Agrawal, ed.; Humana Press: Totowa, 1993, Vol. 20, 63–80.

The phosphotriester approach has been widely used for solution phase synthesis, whereas the phosphoramidite and H-phosphonates strategies have found application mainly in solid phase syntheses. Reese has also reported an approach to the solution phase synthesis of oligonucleotides on H-phosphonate coupling. See, Reese et al. Nucleic Acids Research, 1999, 27, 963–971, and Reese et al. *Biorg. Med. Chem. Lett.* 1997, 7, 2787–2792.

In view of the growing promise of therapeutic, analytical, genomic and other uses of oligonucleotides, it is desirable to produce oligonucleotides in ever increasing quantities. A prerequisite to scaling up phosphoramidite oligonucleotide synthesis is the scale up the process of making phosphorodiamidite precursors. As impurities in the phosphorodiamidite will impact product purity, the phosphorodiamidite must be of exceptional purity. However, the classical methods of purifying phosphorodiamidite, involving distillation at elevated temperature under high vacuum (e.g. 100 degc and 0.5 mm Hg), are not economical for scale-up, as the amount of time required for distillation increases with increasing scale, which in turn leads to degradation of the phosphorodiamidite product.

There is thus a need for a scalable, economical process for purifying phosphorodiamidite.

SUMMARY OF THE INVENTION

The foregoing and other needs are met by embodiments of the present invention, which provide a process for purifying phosphorodiamidite, the process comprising dissolving a crude phosphorodiamidite composition comprising at least one impurity in an apolar organic solvent to form an apolar phase, contacting the apolar phase with a polar phase comprising a polar organic solvent so that at least a portion of the impurity is partitioned from the apolar phase into the polar phase; and separating the polar phase from the apolar phase to produce a purified phosphorodiamidite in an apolar organic solvent.

The foregoing and other needs are met by embodiments of the present invention, which provide a process for manufacturing a purified phosphorodiamidite, the process comprising dissolving a crude phosphorodiamidite comprising at least one impurity in an apolar organic solvent to form an apolar phase, contacting the apolar phase with a polar phase comprising a polar organic solvent so that at least a portion of the impurity is partitioned from the apolar phase into the polar phase; separating the polar phase from the apolar phase; and separating the apolar organic solvent from the phosphorodiamidite to produce the purified phosphorodiamidite.

The foregoing and other needs are met by embodiments of the present invention, which provide a process for manufacturing a purified phosphorodiamidite, the process comprising manufacturing a crude phosphorodiamidite comprising at least one impurity, dissolving the crude phosphorodiamidite in an apolar organic solvent to form an apolar phase, contacting the apolar phase with a polar phase comprising a polar organic solvent so that at least a portion of the impurity is partitioned from the apolar phase into the polar phase; separating the polar phase from the apolar phase; and separating the apolar organic solvent from the phosphorodiamidite to produce the purified phosphorodiamidite.

The foregoing and other needs are further met by embodiments of the present invention, which provide a process for manufacturing a phosphoramidite, the process comprising: dissolving a crude phosphoramidite comprising at least one impurity in an apolar organic solvent to form an apolar phase, contacting the apolar phase with a polar phase comprising a polar organic solvent so that a portion of the impurity partitions from the apolar phase into the polar phase, thereby producing a purified phosphorodiamidite in the apolar phase, and reacting the phosphorodiamidite with a nucleoside to form the phosphoramidite.

The foregoing and other needs are further met by embodiments of the present invention, which provide a process for manufacturing an oligonucleotide, the process comprising: dissolving a crude phosphoramidite comprising at least one impurity in an apolar organic solvent to form an apolar phase, contacting the apolar phase with a polar phase comprising a polar organic solvent so that a portion of the impurity partitions from the apolar phase into the polar phase, thereby producing a purified phosphorodiamidite in the apolar phase, reacting the phosphorodiamidite with a nucleoside to form the phosphoramidite, and further reacting the phosphoramidite with an active hydroxyl group of a nucleoside or an oligonucleotide n-mer to form an oligonucleotide n+1-mer.

In some preferred embodiments of the present invention, a process of the present invention comprises dissolving a crude phosphorodiamidite composition comprising at least one impurity and a compound of formula I:

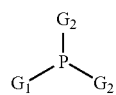

wherein $G_1$ is $OR_1$ or $SR_1$, and $R_1$ is a protecting group and each of $G_2$ and $G_3$ is an amine, in an apolar organic solvent to form an apolar phase; contacting the apolar phase with a polar liquid solution comprising a polar organic solvent so that at least a portion of the impurity partitions from the apolar phase into the polar phase to produce a purified phosphorodiamidite in the apolar phase.

DETAILED DESCRIPTION OF THE INVENTION

The present invention provides an improved process for purifying a phosphorodiamidite, the process comprising dissolving a crude phosphorodiamidite comprising at least one impurity in an apolar organic solvent to form an apolar phase, contacting the apolar phase with a polar phase comprising a polar organic solvent so that at least a portion of the impurity is partitioned from the apolar phase into the polar phase; and separating the polar phase from the apolar phase to produce a purified phosphorodiamidite in an apolar organic solvent.

The inventive process is entirely scalable, being capable of producing 100 g, 1 kg, 10 kg and greater sized batches of phosphorodiamidite of sufficient quality for large-scale oligonucleotide synthesis. In principle the process of the present invention is infinitely scalable, being limited only by the size of reactors available. The inventive process therefore provides phosphorodiamidite having quality suitable for use in producing pharmaceutical-grade oligonucleotides in quantities useful in the pharmaceutical industry.

The inventive processes are sufficiently economical to justify their use in making phosphorodiamidites as precursors for making oligonucleotides, including modified oligonucleotides and oligonucleotide mimetics, for diagnostic, research, analytical and other purposes.

The processes of the present invention may be visualized as comprising a phosphorodiamidite purification process as described herein.

The first step of the purification process comprises dissolving a crude composition comprising phosphorodiamidite (crude phosphorodiamidite) and at least one impurity in an apolar organic solvent to form an apolar phase. There is thus formed an apolar phase comprising the phosphorodiamidite and at least one impurity.

The second step of the purification process comprises contacting the apolar phase with a polar phase comprising at least one polar organic solvent.

As the apolar and polar phases are contacted, at least a portion of at least one impurity in the apolar phase migrates into the polar phase, thereby increasing the purity of the phosphorodiamidite in the apolar phase. The apolar and polar phases may then be separated from one another, whereby an apolar solution comprising purified phosphorodiamidite is produced. The apolar organic solvent may then be removed from the phosphorodiamidite to produce a purified phosphorodiamidite solid, or the apolar solution comprising purified phosphorodiamidite may be used in further processing.

The crude composition comprising phosphorodiamidite and at least one impurity may be obtained by a conventional method as described herein. The term impurity is defined herein. The apolar organic solvent is an apolar organic solvent in which the phosphorodiamidite and the impurity are soluble. The polar phase comprises a polar organic solvent, and optionally comprises water. The purified phosphorodiamidite contains less of said impurity, relative to the amount of phosphorodiamidite, than the crude phosphorodiamidite.

The person skilled in the art will appreciate that the apolar organic solvent and the polar phase should be selected such that optimally large amount of impurity partitions from the apolar phase into the polar phase, while at the same time the optimally small amount of phosphorodiamidite partitions from the apolar phase into the polar phase.

Suitable apolar organic solvents include, but are not limited to, alkanes, such as hexanes, heptane, cyclohexane and mineral spirits, and aryl compounds such as toluene and xylenes. Mixtures of apolar organic compounds may also be used in accordance with the present invention. For instance, one or more lower alkane compounds may act as a co-solvent with one or more aryl compounds, such as toluene. The person skilled in the art will recognize that the apolar organic solvent should be one which dissolves all the components of the crude phosphorodiamidite (containing at least one impurity).

Suitable polar organic solvents include, but are not limited to, acetonitrile, N,N-dimethylformamide (DMF), ethylene glycol, and glycerol. Other suitable polar organic solvents include: acetamide, ethylene diamine, N,N,-dimethylacetamide, N-methylacetamide, N-methylformamide, dimethylsulfoxide, ethanolamine, diethanolamine, triethanolamine, caprolactam, 3-hydroxypropiononitrile, hexamethylphosphoric triamide, dimethylurea, tetramethylurea, 2-pyrrolidinone, N-methylpyrrolidinone and 2-imidazolidone. The polar phase may also include water as a co-solvent. While not wishing to be bound by theory, it is believed that the addition of water as a co-solvent in the polar phase increases the polarity of the polar phase, thereby making the polar phase more selective for polar impurities. Additionally, it is also possible to combine more polar organic solvents with less polar organic solvents to adjust the polarity of the polar phase so that it is selective for certain impurities. Of course it is also possible to combine two or more polar organic solvents and water to form a polar phase having a particular polarity necessary for obtaining the selectivity necessary for a particular mixture of phosphoramidite and impurity. The person skilled in the art will recognize that the polar phase should be one in which impurities present in the crude phosphoramidite are soluble. It is preferred that the solubility of impurities in the polar phase be greater than the solubility of said impurities in the apolar phase. In other words, it is desirable that, with respect to impurities, the partition coefficient between the apolar and polar phases should favor the polar phase.

At a minimum, the impurity should be more soluble in the polar phase than is the phosphorodiamidite. It is preferred that the impurity be significantly more soluble in the polar phase than is the phosphorodiamidite. While reference is made here to "the impurity" it is to be understood that more than one non-phosphorodiamidite compound may be encompassed within the meaning of the term "impurity".

The polar phase should also be one in which the phosphorodiamidite is minimally soluble. While it is tolerable in some embodiments for the phosphorodiamidite to be soluble in the polar phase to a limited extent, it is important for the sake of conserving phosphorodiamidite product that it not be so soluble that repeated washings would result in an uneconomical loss of phosphorodiamidite into the polar phase.

The effectiveness of the present purification process is affected by the partition coefficient of each component of the crude phosphorodiamidite composition between the apolar and polar phases. It is thus advantageous to choose the apolar phase and the polar phase to maximize partitioning of the phosphorodiamidite into the apolar phase and to maximize partitioning of one or more impurities into the polar phase. Thus, the apolar phase and the polar phase should be chosen in apolar-polar solvent pairs. Suitable apolar-polar solvent pairs include apolar alkanes paired with polar acetonitrile (optionally including water), DMF, ethylene glycol, or mixtures thereof. Other suitable apolar-polar solvent pairs include apolar toluene paired with polar ethylene glycol, glycerol, DMF or mixtures thereof. Other apolar-polar solvent pairs are contemplated as being within the scope of the present invention, so long as they meet the relative partition coefficient criteria described above. Suitable apolar-polar phase pairs include alkanes (apolar)—acetonitrile/water (polar). Suitable apolar-polar pairs include alkanes (apolar)—acetonitrile (optionally with water as a co-solvent; polar). Especially suitable alkanes include hexanes, heptanes, cyclohexane, etc. An especially suitable apolar-polar solvent pair is hexanes (apolar)—acetonitrile/water (polar). Another especially suitable apolar-polar solvent pair is heptane (apolar)—acetonitrile/water (polar).

A goal of the present invention is to purify phosphorodiamidite—i.e. to separate phosphorodiamidite from at least a portion of the impurity mixed therewith. Accordingly, the apolar phase comprising purified phosphorodiamidite is advantageously separated from the polar phase comprising at least one impurity. In this regard, it is advantageous that the polar phase apolar phase and the polar phase be separable, meaning that the two phases should be relatively immiscible. Although it is to be expected that some of the apolar organic solvent may dissolve in the polar phase, some of the polar organic solvent may dissolve in the apolar phase, or both, nonetheless two distinct phases should form, one of which is primarily an apolar phase and the other of which is a polar phase. The term "separable" as used with respect to the present invention means that two distinct phases—apolar and polar—form when using a particular apolar-polar solvent pair.

In some embodiments of the present invention, the phosphorodiamidite is the most hydrophobic compound in the apolar phase. In such cases, one may advantageously select a polar phase solvent that is just polar enough to dissolve the least polar impurity in the crude phosphorodiamidite, while leaving the phosphorodiamidite in the apolar phase.

In some embodiments of the present invention, additional steps may be employed. In some cases, especially where water is used as a co-solvent in the polar phase, and where the phosphorodiamidite will remain in the apolar phase for an extended period after separation, it may be desirable to employ a drying step to remove water from the apolar phase after the two phases are separated. Conventional drying agents may be employed for this purpose.

The apolar and polar phases must be contacted in order for mass transfer to occur between the two phases. Contact between the apolar and polar phases can be effected by one or more conventional methods. The means of contacting the two phases is not critical to the present invention. In general, the two phases are placed in a vessel, such as a separatory funnel, a rotary evaporator or a mixing tank, after which the two phases are agitated to maximize the contact surface area between the two phases in order to accelerate the kinetics of mass transfer between the two phases. Agitation may be accomplished by a suitable method, such as shaking (in the case of a laboratory separatory funnel) or rotation (in the case of a rotary evaporator) or mixing (in the case of the mixing tank). After a period of agitation, the two phases are allowed to settle, during which time the apolar and polar phases separate from each other, the denser occupying the space at the bottom of the vessel and the less dense phase forming a layer on top of the denser phase. The two phases may then be separated from one another by suitable methods, such as by decanting off the less dense phase from the top, or by draining the denser phase from the bottom. In some embodiments of the present invention, the polar phase is the denser phase.

Suitable devices for effecting mixing and separation include separation funnels (especially in laboratory-scale procedures) and reaction kettles (having volumes of e.g. 50, 100 or 500 liters and up). In some embodiments of the invention, the mixing and separation device is adapted for continuous washing of the apolar phase with the polar phase. In other embodiments, multiple washings may be effected by separate stages of mixing, settling and separation. Other conventional separation methods may be used within the scope of the invention.

The third step of the purification process comprises separating the apolar organic solvent and the polar phase. In so doing, the desired product, phosphorodiamidite, is isolated in the apolar phase. Impurities are isolated in the polar phase, and are thus effectively separated from the desired phosphorodiamidite product.

Separation of the apolar phase and the polar phase may be accomplished by a conventional separation process, such as by decanting, etc. The person having skill in the art will recognize that the particular separation method chosen will depend upon the scale of the separation. Laboratory-scale separation may be effected, for instance, using a separatory funnel, whereas larger-scale separations are more conveniently carried out in large reaction kettles. The skilled person will choose appropriately-sized separation vessels, taking into consideration the amount of phosphorodiamidite to be purified, the volume of the polar and apolar phases, time constraints, etc.

The phosphorodiamidite that is isolated in the apolar phase is referred to herein as a purified phosphorodiamidite. The purified phosphorodiamidite is characterized by a higher percent purity than the crude phosphorodiamidite. Although the purified phosphorodiamidite inevitably contains some level of impurities, which may or may not be detectable, it is to be understood that purified phosphorodiamidite, as used herein, is the product produced by the purification process described herein, which has a higher degree of purity than the crude phosphorodiamidite.

The term phosphorodiamidite refers generally to a phosphorus atom in the P(III) oxidation state that is covalently bonded to two amino groups and one member of the group of —OH, —O-Prot, —SH or —SProt, wherein Prot is a protecting group. In some embodiments of the present invention, the phosphorodiamidite comprises a P(III) phosphorus, two amino groups and O-Prot, wherein Prot is a phosphorus protecting group. In the context of the present invention, "phosphorus protecting group" means a protecting group that is removable under selective conditions, and that prevents substitution on, or interference by, a hydroxy- or thiol-group on phosphorus (whether in the P(III) or P(V) oxidation state). In preferred embodiments of the invention, the selective conditions under which suitable phosphorus protective groups are removed are distinct from the conditions under which 5'-, 3'- or 2'-protective groups, base protective groups, etc. are removed from a nucleoside.

As used herein, the term phosphorodiamidite, by itself, refers generally to both purified and crude phosphorodiamidite.

The term "crude phosphorodiamidite" includes phosphorodiamidite containing one or more non-phosphorodiamidite compounds, or impurities, such as side products, residual reagent, residual starting material, residual solvent and/or other impurities introduced by one or more steps of a process of manufacturing phosphorodiamidite. Impurities include those present in the starting materials, reagents and solvents used in the production of the starting materials, reagents and solvents used to produce the crude phosphorodiamidite, as well as unreacted reagents, starting materials, catalysts, side-products, etc. Impurities may also be introduced by exogenous sources, such as in the transportation of phosphorodiamidite. Thus, crude phosphorodiamidite refers to phosphorodiamidite that contains one or more non-phosphorodiamidite compound (contaminant) that can be removed by a purification process of the present invention.

A preferred genus of phosphorodiamidite that may be purified by a process of the present invention is illustrated in formula I:

wherein $G_1$ is $OR_1$ or $SR_1$, and $R_1$ is a phosphorus protecting group; and each of $G_2$ and $G_3$ is an amine, bound to the P through an amine nitrogen.

Suitable phosphorus protecting groups represented by $R_1$ include alkyl, such as methyl, taught by Caruthers et al. U.S. Pat. No. 4,458,066; cyanoalkyl groups and isothiocyanoalkyl groups, such as cyanoethyl and isothiocyanoalkyl taught by Köster et al, U.S. Re. 34,069; silylalkyl groups, such as those taught by Ravikumar et al. U.S. Pat. Nos. 5,847,106, 6,124,450, 5,614,621 and 5,847,106; an optionally substituted alkenyl such as those taught by Ravikumar et al., U.S. Pat. Nos. 5,705,621, 6,051,699; arylcarbonyloxyalkyl, arylthiocarbonyl-oxyalkyl, arylcarbonylaminoalkyl, arylthiocarbonylaminoalkyl, aryloxycarbonyloxyalkyl, aryloxythiocarbonyloxyalkyl, aryloxycarbonylaminoalkyl, aryloxythiocarbonylaminoalkyl, arylthiocarbonyloxyalkyl, arylthiothiocarbonyloxyalkyl, arylthiocarbonylaminoalkyl, arylthiothiocarbonylaminoalkyl, all as disclosed in Guzaev et al., U.S. Pat. No. 6,121,437; carbonylaminoalkyl, such as those taught in Cheruvallath et al., U.S. Pat. Nos. 5,760,209, 5,783,690; aralkyl as taught by Yau, U.S. Pat. No. 5,210,264; substituted aralkyl, such as those discussed in Capaldi et al., U.S. Pat. Nos. 6,020,475, 6,160,152; optionally substituted alkenyl, such as those disclosed by Manoharan in U.S. Pat. No. 6,169,177; substituted aryloxyalkyl or arylthioalkyl as taught by Cheruvallath et al., U.S. Pat. No. 6,326,748, each of which is expressly incorporated herein by reference.

Suitable amines represented by $G_2$ and $G_3$ include secondary amines such as heteroaryl amines, including tetrazole, substituted imidazoles such as nitroimidazole, indole, pyrazole, imidazole, benzimidazole, isoindole, pyrrole, triazole, dioxazole and similar heterocyclic amines, as well as analogs and homologs thereof, all taught in Caruthers et al., U.S. Pat. No. 4,500,707, amines of the formula $NR_2R_3$, wherein each $R_2$ and $R_3$ is independently alkyl, aryl, aralkyl, or cycloalkyl; or $R_2$ and $R_3$ are taken together to form a saturated or unsaturated heterocyclyl group containing one or more nitrogen atoms and optionally one or more additional atoms selected from the group consisting of nitrogen, oxygen and sulfur, all as disclosed by Caruthers et al., U.S. Pat. No. 4,973,679.

In some embodiments of the invention, suitable amines represented by $G_1$ are represented by $NR_2R_3$, wherein $R_2$ and $R_3$ are independently alkyl, substituted alkyl, alkenyl, substituted alkenyl, alkynyl, substituted alkynyl, cycloalkyl, alkanoyl (i.e. alkylcarbonyl), substituted alkanoyl, alkylsulfonyl, substituted alkylsulfonyl, substituted cycloalkyl, cycloalkenyl, substituted cycloalkenyl, aryl, substituted aryl, heterocyclo, substituted heterocyclo, aralkyl, substituted aralkyl, heterocyclolalkyl, substituted heterocycloalkyl; or $R_2$ and $R_3$ together with the nitrogen to which they are attached form an optionally substituted heterocyclic ring.

Alkyl, alkenyl and alkynyl groups mentioned above, as well as the hydrocarbyl portion of alkanoyl and alkylsulfonyl groups mentioned above, have carbon chain sizes in the range of about $C_1$ to about $C_{12}$, and the chain may be branched, where possible, or straight-chain. Among the alkyl, alkenyl and alkynyl groups that may be mentioned are methyl, ethyl, n-propyl, isopropyl, n-butyl, t-butyl, s-butyl, isobutyl, n-pentyl, n-hexyl, hex-2-yl, ethenyl, propen-2-yl, propen-1-yl, butynyl, etc. Among the alkanoyl groups that may be mentioned are ethanoyl ($CH_3C(O)$—), triskaidecanoyl ($CH_3(CH_2)_{11}C(O)$—), etc. Among the sulfonyl groups that may be mentioned are methanesulfonyl ($CH_3SO_2$—) and dodecanesulfonyl ($CH_3(CH_2)_{11}SO_2$—), etc.

Cycloalkyl and cycloalkenyl groups, are in the range of $C_3$ to about $C_{12}$, with ring sizes in the range of about $C_3$ to about $C_7$ being especially preferred. Among the cycloalkyl groups that are within the scope of the present invention are cyclopentyl, cyclohexyl and cycloheptyl. Included within the meaning of cycloalkenyl groups are those cyclic groups that are non-aryl and have two, three or more unsaturations in the ring. Among the cycloalkenyl rings that may be mentioned include cyclopentenyl, cyclopenta-1,3-dienyl, cyclohexenyl, cyclohexa-1,3-dienyl, cycloheptenyl, cyclohepta-1,3-dienyl and cyclohepta-1,4-dienyl. The carbocyclic rings included within this definition may be fused to one or more other carbocyclic rings, one or more heterocyclic rings, or may be bridged or spiro, bicyclic or polycyclic. Representative polycyclic cycloalkyl rings included in this definition are bridged cyclic alkanes such as adamantane, norpinane and bicyclo[2.2.1]heptane, as well as spiro alkanes such as spiropentane.

Heterocyclic ring substituents include 3 to 12 membered, saturated or unsaturated, monocyclic, bicyclic or polycyclic, substituted or unsubstituted rings or ring systems. Exemplary heterocyclic ring substituents include imidazolyl, morpholino, furanyl, pyranyl, oxazolyl, pyridinyl, quinazolinyl, pyrimidinyl, purinyl, etc.

Where $R_2$ and $R_3$ form a heterocyclo ring, the ring may be saturated, unsaturated or aromatic, and may have, in addition to the nitrogen to which $R_2$ and $R_3$ are joined, one or more additional heteroatoms. Such other heteroatoms include N, S and O. Suitable ring sizes for such heterocyclo rings are from 3 to about 12 ring members. Preferred ring sizes are from about 5 to about 7 ring members. Additionally, the ring may form a bicyclo or polycyclo ring system. Particular heterocyclo rings that may be mentioned in this context include morpholino, thiomorpholino, piperazinyl, N-methylpiperazino, pyrrolidino, piperidino, homopiperidino, homomorpholino, homothiomorpholino, and their unsaturated, bridged, and ring-fused counterparts. Additional members of this group include those taught by Caruthers et al. in U.S. Pat. No. 4,500,707.

Suitable substituents include those substituents that do not interfere with the phosphorylation reaction.

In some embodiments of the present invention, the phosphorodiamidite is represented by formula II

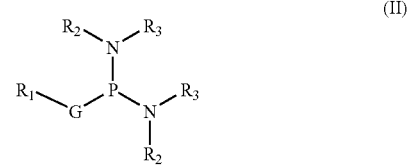

wherein G is O or S; $R_1$ represents a phosphorus protecting group as described herein; and each $NR_2R_3$ independently represents an amine as defined. In specific embodiments of the present invention, each $R_2$ and $R_3$ independently represents an unsubstituted alkyl, a substituted alkyl, an unsubstituted alkenyl, a substituted alkenyl, an unsubstituted alkynyl, a substituted alkynyl, an unsubstituted aryl, a substituted aryl, an unsubstituted cycloalkyl, a substituted cycloalkyl, an unsubstituted cycloalkenyl, a substituted cycloalkenyl, an unsubstituted heterocyclo, or a substituted heterocyclo; or $R_2$ and $R_3$, together with the nitrogen to which they are attached, form a nitrogen-containing heterocyclyl ring, which is optionally substituted and which is optionally unsaturated.

In certain embodiments of the present invention, the phosphorodiamidite to be purified can be represented by formula III:

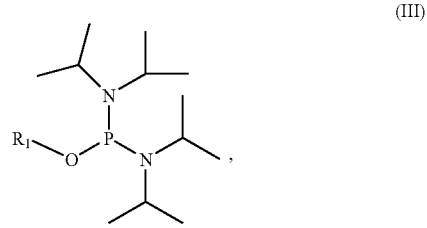

wherein $R_1$ is a phosphorus protecting group as described herein.

In some embodiments of the present invention, the phosphorodiamidite to be purified can be represented by formula IV:

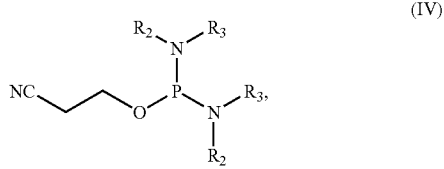

(IV)

wherein each of $NR_2R_3$ is independently an amine as defined herein.

In particular embodiments of the present invention, the phosphorodiamidite to be purified can be represented by formula V:

The crude phosphorodiamidite, which is the starting material for the purification process of the present invention, may be made by a conventional process, such as that set forth in Köster et al., U.S. Re. 34,069 or Caruthers et al., U.S. Pat. Nos. 4,973,679 or 4,500,707, each of which is expressly incorporated herein by reference. The source of crude phosphorodiamidite is not critical to the present invention. In some embodiments the process of making the phosphorodiamidite produces impurities in the crude phosphorodiamidite such that the phosphorodiamidite is the most apolar compound in the crude phosphorodiamidite composition. However, in other embodiments of the present invention, both relatively apolar and relatively polar impurities are present in the crude phosphorodiamidite.

A typical process for making phosphorodiamidite is illustrated in synthetic Scheme 1, below.

SCHEME 1

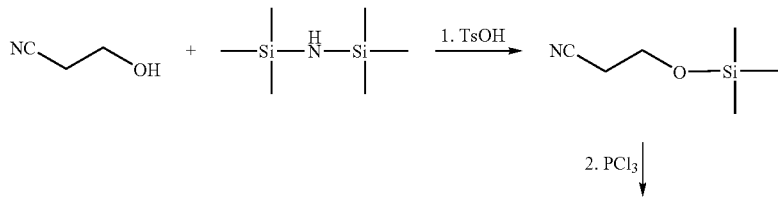

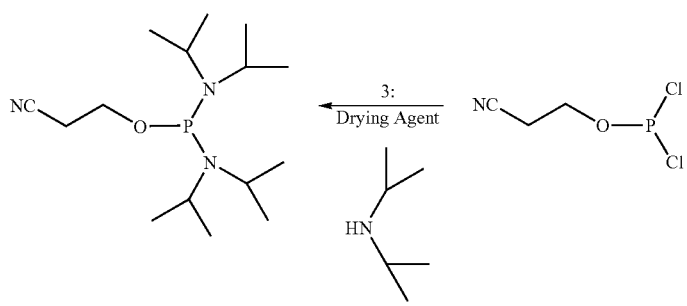

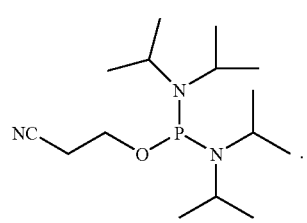

(V)

In the step 1., 3-hydroxypropionitrile is reacted with HMDS, optionally in the presence of an acid, such as p-toluenesulfonic acid (TsOH) or some other suitable acid, which acts as a catalyst. Other suitable acids include trifluoroacetic acid, ammonium chloride and ammonium sulfate. While not wishing to be bound by theory, it is believed that acids having pKa values similar to those of the acids named above will act as suitable catalysts. The reaction between 3-hydroxypropionitrile and HMDS can be carried out in the absence of catalyst, however it is preferred to use a catalyst. Also, the first step may be carried out in a solvent, but it is preferred to carry out the reaction without solvent. The product of step 1, 3-trimethylsilanyloxypropionitrile, is a liquid at room temperature.

It has been discovered that a portion of the distillate from step 1 (the HMDS reaction with 3-hydroxypropionitrile) may be conveniently recycled. In a suitable method, HMDS, TsOH, 3-hydroxypropionitrile, and optionally an early fraction from a previous run, are combined and stirred at elevated temperature. An early fraction from this distillation is then collected and set aside for recycling in a later run. A later fraction, containing the 3-trimethylsilanyloxypropionitrile (($CH_3$)$_3$Si—OCH$_2$CH$_2$CN), is then collected for further processing (i.e. reaction with PCl$_3$, etc.). A residue, which is left in the distillation vessel, is discarded as waste.

In some embodiments of the present invention, HMDS, TsOH and 3-hydroxypropionitrile are combined, optionally with an early fraction from a previous run, and are stirred at an elevated temperature. A first fraction is collected and discarded, a second fraction is then collected and saved for recycling, and a third fraction, containing the desired 3-trimethylsilanyloxypropionitrile intermediate, is then collected until a small volume remains in the reaction vessel. The residual small volume that is left in the distillation vessel is then discarded.

The person skilled in the art will recognize that the exact volumes of distillate collected in each fraction will vary from batch to batch, depending upon such things as batch size, reaction efficiency, reagent purity, etc. In an illustrative embodiment, about 15.5 L of HMDS is combined with about 10 Kg of 3-hydroxypropionitrile and about 10 g of toluenesulfonic acid at 60–80° C. for approximately 1 h. An early fraction from another batch of approximately 4 L in volume is then added and the reaction is distilled at reduced pressure. The first fraction (~2 L) is collected and discarded. The second fraction (~4 L) is collected and saved for recycling in the next HMDS reaction run. The third fraction (product, ~22 L) is then collected until ~5 L remains in the distillation vessel. The person skilled in the art will recognize that the above values must be scaled in proportion to the quantity of reagents, recycled fraction, and catalyst present in the distillation vessel. The person skilled in the art will also recognize that some variation in fraction volume, on the order of about ±1% to about ±25% variation in fraction volume, may be necessary in order to optimize yield and purity of the product. It is considered within the skill of the artisan in this art to optimize fraction volumes, given the foregoing description of the inventive concept.

In step 2., the 3-trimethylsilanyloxypropionitrile (silanyl ether) is reacted with phosphorus trichloride (PCl$_3$). Care should be taken to add the silyl ether to PCl$_3$, and not the other way around. The reaction may be carried out in a solvent or without solvent, but the latter is preferred. The silyl ether is then co-evaporated with hexanes to produce a colorless liquid.

In step 3., an amine, such as diisopropylamine, is reacted with the product of step 2, optionally in the presence of a drying agent. The drying agent may be a water scavenger, or a scavenger of both water and alcohols. In some embodiments, a water scavenger is sufficient, and in such cases a drying agent such as K$_2$CO$_3$ will suffice. In other embodiments, e.g. where there are alcohols such as isopropanol (which is in some commercially available diisopropylamine as a contaminant) present in the solution, a scavenger of water and alcohols, such as POCl$_3$, will be advantageously employed. While other scavengers of water and alcohols, such as acetyl chloride, SOCl$_2$, oxayl chloride, etc. may be used, POCl$_3$ is preferred, as its presence or absence in later steps may be easily monitored by $^{31}$P NMR.

The reaction of step 3. may be carried out in the presence of a suitable solvent, such as alkanes, especially hexanes, heptane. After the reaction is completed, the reaction mixture is extracted with a polar solvent (such as water, acetonitrile, or mixtures thereof). The product phosphorodiamidite is obtained after evaporation of solvent as a colorless to pale yellow liquid.

Other processes of making crude phosphorodiamidite are set forth in, for example, Köster et al. RE 34,069, which is expressly incorporated herein by reference.

A general process for synthesizing crude phosphorodiamidite of formula I, above, is thus depicted in synthetic Scheme 2.

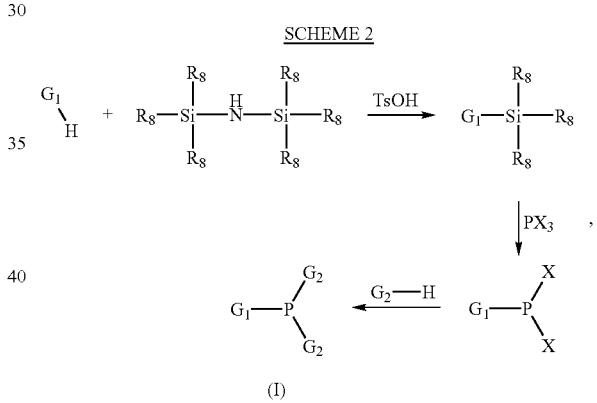

SCHEME 2 wherein each X is independently a leaving group, such as a halide (e.g. Cl, Br, I) or other suitable leaving group, each R$_8$ is an alkyl group, and G$_1$ and G$_2$ are as defined herein. As each G$_2$ is independently an N-linked amine, it is possible for separate amines to be incorporated into the compound of formula (I), either simultaneously or sequentially. In certain embodiments of the present invention, the G$_2$ amines are identical.

As used in the context of R$_8$ only, the term "alkyl" includes branched and straight-chain C$_1$–C$_{12}$ alkyl. As used in the context of R$_8$, the term "lower alkyl" includes branched and straight-chain C$_1$–C$_6$ alkyl. Groups that are included within the scope of R$_8$ include methyl, ethyl, n-propyl, isopropyl, n-butyl, s-butyl, t-butyl, isobutyl, n-pentyl, n-hexyl, and n-dodecyl.

When the phosphorodiamidite has a structure of formula II, the process for making the phosphorodiamidite is shown in synthetic Scheme 3.

SCHEME 3

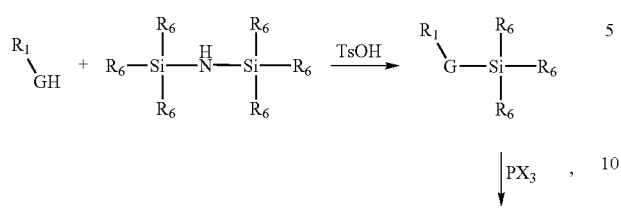

SCHEME 4

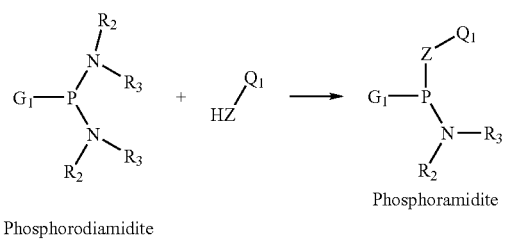

Phosphorodiamidite        Phosphoramidite

SCHEME 4A

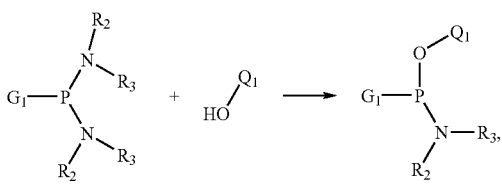

wherein $R_1$ and $NR_2R_3$ are as defined herein and each $R_6$ is independently alkyl, as defined under $R_8$ above. In some embodiments of the present invention each $HNR_2R_3$ is di-isopropylamine. In some embodiments of the present invention, G is O and $R_1$ is methyl or cyanoethyl. In particular embodiments of the present invention, G is O, $R_1$ is methyl or cyanoethyl and each $NR_2R_3$ is diisopropylamino.

Crude phosphorodiamidite may be obtained by multiple pathways, such as by obtaining crude phosphorodiamidite via diverse synthetic processes. The purification process of the present invention is applicable to crude phosphorodiamidite in general, without regard to the synthetic pathway or conditions employed in its manufacture. In some embodiments of the present invention, crude phosphorodiamidite may be obtained from more than one producer of phosphorodiamidite, combined in a single batch, and purified to produce a purified phosphorodiamidite that meets predetermined quality specifications, such as low impurity levels. In other embodiments of the present invention, the crude phosphorodiamidite may be purified to form separate lots of purified phosphorodiamidite, and then combined prior to further processing as described herein. In still other embodiments of the present invention, crude phosphorodiamidite may be produced by a single source.

In preferred embodiments of the present invention, the phosphorodiamidite is obtained by a process essentially similar to that set forth in one of Schemes 1–3 above.

Phosphorodiamidite can be used in the synthesis of phosphoramidite, which is in turn useful for coupling a monomer, such as a nucleoside monomer, to a compound containing an active hydroxyl group, such as a nucleotide.

An exemplary method of making phosphoramidite is illustrated in Schemes 4 and 4A below:

wherein $G_1$, Prot and $NR_2R_3$ are defined above and $Q_1$ is a monomer. The reaction of Scheme 4 is carried out in a suitable solvent, such as acetonitrile, dichloromethane or DMF, and in the presence of a weak acid, such as tetrazole or a mixture of tetrazole and an imidazole. In reaction Scheme 4, ZH represents a moiety including an active oxygen, sulfur, amine or other substituent that may be on a monomer. In some embodiments, Z includes an alkylene spacer between the monomer unit and the active oxygen, sulfur, amine, etc. Suitable examples of the group —ZH include: —OH, —SH, —$NH_2$, —$CH_2$—OH, —$CH_2$—SH and —$CH_2$—$NH_2$. Other values of Z are more fully described herein.

In some embodiments of the present invention, the reaction is carried out in a DMF, in the presence of a mixture of tetrazole and N-methylimidazole. Other suitable catalysts are set forth by Just et al. in U.S. Pat. No. 5,734,041 and Sanghvi et al. U.S. Pat. No. 6,274,725, incorporated herein by reference.

In some embodiments, the ratio of phosphorodiamidite to nucleoside is about 1:1 or greater. In some other embodiments, the ratio of phosphorodiamidite to nucleoside is about 1.05:1 or greater. In further embodiments, the ratio is about 1.5:1 or greater.

In general $Q_1$ may be any monomer that has an OH group as a substituent. Thus, $Q_1$ may be a drug moiety, or a nucleoside monomer, a nucleotide, a nucleotide oligomer, etc. Included in the term "nucleotide oligomer" are oligomers having phosphate or phosphorothioate in the backbone, as well as alternative backbone structures, including amide, peptide nucleic acid, and other backbones, as described more fully herein. In some embodiments of the present invention $Q_1$ is a monomer such as:

wherein $Q_1$ is a suitable organic radical, such as a sugar, a steroid, or other suitable radical to form a compound of formula VI, below:

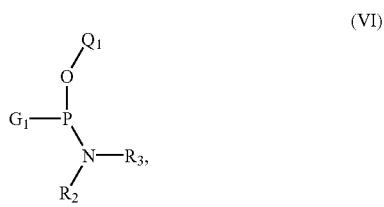

wherein $Q_1$ is an organic radical and $G_1$ and $NR_2R_3$ are as defined herein.

A purified phosphorodiamidite of the present invention may be used to prepare an oligonucleotide by the methodology set forth in Schemes 5 and 5A, below.

SCHEME 5

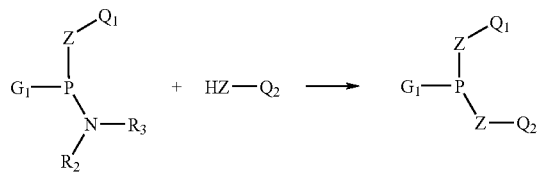

Scheme 5

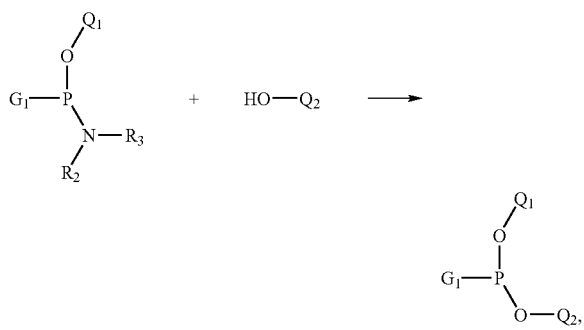

wherein $Q_1$ is an organic radical, such as a nucleotide or nucleoside monomer, $G_1$ and $NR_2R_3$ are as defined herein, and $Q_2$—OH is a monomer or an oligomer. The group ZH (or HZ, per Scheme 5A) represents a moiety including an active oxygen, sulfur, amine or other substituent that may be on a monomer. In some embodiments, Z includes an alkylene spacer between the monomer unit and the active oxygen, sulfur, amine, etc. Suitable examples of ZH include: —OH, —SH, —NH$_2$, —CH$_2$—OH, —CH$_2$—SH and —CH$_2$—NH$_2$. Other suitable values for ZH are more fully described herein.

In some embodiments of the present invention, $Q_2$ is a nascent oligomer, either in solution phase or bound to a solid support. A nascent oligomer includes a monomer bonded to a solid support, a protected monomer in solution phase, an oligomer bonded to a solid support or a protected oligomer in solution. A monomer includes a deoxyribonucleic acid monomer, a ribonucleic acid monomer, an arabinonucleic acid monomer, a substituted deoxyribonucleic acid monomer, (in which the substituent may be in either the ribo- or arabino-conformation), a nucleic acid analog, such as one in which the ribose sugar is replaced with an erythrose sugar, including a 2'-deoxy or a 2'-deoxy-2'-substituted or unsubstituted erythrose sugar, a cyclopentane ring, a pyrrolidine ring, a tetrahydrothiophene ring, etc.

When the nascent oligomer is support-bound, it is advantageously bound to a solid support via a linking moiety. Suitable linking moieties are set forth, for example by Pon et al. in U.S. Pat. Nos. 6,015,895 and 6,043,353.

When the nascent oligomer is in solution phase, it generally has a 3'- or 5'-hydroxyl group that must be protected by a suitable hydroxyl protecting group.

A hydroxyl protecting group is a protecting group that is labile under selected conditions, and the protects the hydroxyl group from participating in, or interfering with, the reaction between the phosphoramidite and an unprotected hydroxyl group of the monomer or oligomer. Where the oligonucleotide is bound to a solid support during synthesis, a suitable hydroxyl protecting group will be labile under acidic conditions, such as in the presence of trichloroacetic acid. A suitable protecting group is the 4,4'-dimethoxytriphenylmethyl (DMT) group. Where the oligonucleotide is not bound to a solid support, there will be a hydroxyl protecting group on each end of the oligonucleotide. In some embodiments, the hydroxyl on the growing end of the oligonucleotide will be labile under certain conditions, whereas the hydroxyl on the opposite end of the oligonucleotide, i.e. the non-growing end, will be labile under different conditions. For example, where the oligonucleotide is synthesized from the 3'- to the 5'-direction, the 3'-hydroxyl may be protected with a base-labile protecting group, while the 5'-hydroxyl is protected with an acid-labile protecting group. This arrangement is also advantageous where the nucleobases are protected with protecting groups that may be removed under basic (i.e. elevated pH) conditions. Such conditions are set forth, e.g., in the Köster and Caruthers patents cited herein.

A preferred use of phosphorodiamidite of the invention, and thus of the phosphoramidite produced thereby, is in the manufacture of oligonucleotides. An illustrative process of manufacturing an oligonucleotide of the present invention is set forth in Scheme 6, below.

SCHEME 6

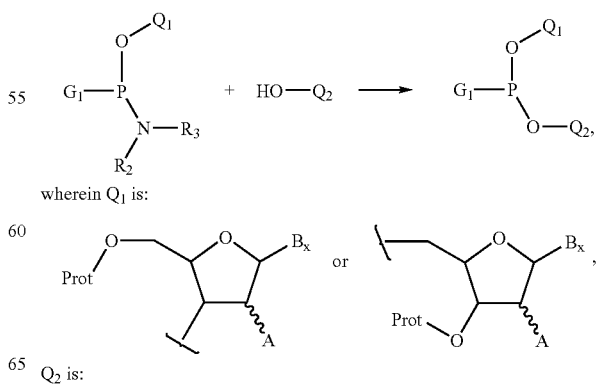

wherein $Q_1$ is:

$Q_2$ is:

-continued

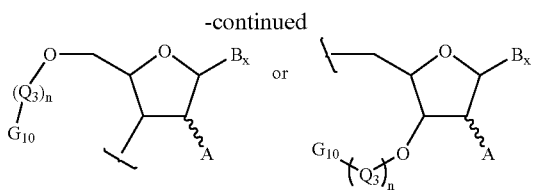

and each $Q_3$ is independently:

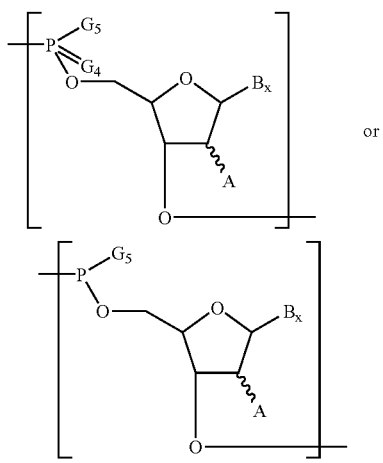

wherein, in each of the above sub-formulae, where appropriate, $G_1$ is $OR_1$ or $SR_1$, $NR_2R_3$ is an amine, A is a sugar substituent (in the ribo- or arabino-configuration, as described more fully herein), $B_x$ is a nucleobase, $G_4$ is O or S, $G_5$ is OH, SH, $OR_1$ or $SR_1$, $R_1$ is a phosphorus protecting group, n is 0 or a positive integer, Prot is a hydroxyl protecting group, and $G_{10}$ is Prot or a linking group to a Solid Support.

As used herein, a nucleobase is a group capable of binding, whether via Watson-Crick binding, Hoogstein binding, clamp-type binding, or non-specific binding to a complementary base of an oligonucleotide. Included within the meaning of "nucleobase" is a heterocyclic base moiety, (also referred to in the art simply as a "base"). Heterocyclic bases useful in the present invention include both naturally and non-naturally occurring nucleobases. The heterocyclic base moiety further may be protected wherein one or more functionalities of the base bears a protecting group. As used herein, "unmodified" or "natural" nucleobases include the purine bases adenine and guanine, and the pyrimidine bases thymine, cytosine and uracil. Modified nucleobases include other synthetic and natural nucleobases such as 5-methylcytosine, 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil, 5-propynyl cytosine, 6-aza uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the Concise Encyclopedia Of Polymer Science And Engineering, pages 858–859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289–302, Crooke, S. T. and Lebleu, B., ed., CRC Press, 1993.

Exemplary nucleobases that are suitable for making oligonucleotides of the present invention include: 2,6-diaminopurine, 6-phenyllumazine, 7-(4-biphenyl)lumazine, 5-methylcytosine, 5-propynyluracil, 5-propynylcytosine, 5-(thiazol-2-yl)uracil; 5-(5-methyl-2-yl)uracil; guanine, cytosine, thymine, uracil, adenine, 7-deazaguanine; tubercine (7-deazaadenine); 7-deaza-7-methylguanine; 7-deaza-7-iodoguanine; 7-deaza-7-bromoguanine; 7-(propyn-1-yl)-7-deazaguanine; 7-(hex-1-ynyl)-7-deazaguanine; 7-iodo-7-deaza-2-aminoadenine; 7-(prop-1-ynyl)-7-deaza-2-aminoadenine; 7-cyano-7-deaza-2-aminoadenine; 7-(prop-1-ynyl)-7-deazadenine; 7-ethynyl-7-deazadenine; 7-bromo-7-deazadenine; 7-chloro-7-deazadenine; 7-methyl-7-deazadenine; 7-deaza-8-azadenine; 7-deaza-8-azaguanine; spermine-conjugated guanine; 5-(N-aminohexyl)carbamoyluracil; triaminoalkylamidouracil; 7-(3-aminopropyn-1-yl)-7-deazadenine; 3-aminopropyn-1-yluracil; 2,7-dioxopyridopyrimidine; phenoxazinopyrimidine; phenothiazinopyrimidine; tetracyclic deazadenine; 2-thiothymine; 2-thiouracil; hypoxanthine; xanthine; pyrrolopyrimidinone; N-choloroethylcytosine; haloacetylcytosine; $N^4,N^4$-ethanocytosine; $N^2$-imidazolylpropylguanine; $N^2$-imidazolylpropyl-2-aminoadenine; 5-methyl-$N^4$-(1-pyrenylmethyl)cytosine; $N^4$-diphenylether-5-methylcytidine; Aminoethoxyphenoxazinopyrimidine-2-one. See P. Herdewijn, Antisense & Nucleic Acid Drug Development, 10:297–310 (2000).

Certain heterocyclic base moieties are particularly useful for increasing the binding affinity of the oligomeric compounds of the invention to complementary targets. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Id., pages 276–278) and are presently preferred base substitutions, even more particularly when combined with selected 2'-sugar modifications such as 2'-methoxyethyl groups.

Representative United States patents that teach the preparation of heterocyclic base moieties (modified nucleobases) include, but are not limited to, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, certain of which are commonly owned, and each of which is herein incorporated by reference, and commonly owned U.S. patent application Ser. No. 08/762,587, filed on Dec. 10, 1996, also herein incorporated by reference.

Heterocyclic base moieties can be further substituted. Suitable base substituents include aminooxy substituents, set forth in U.S. Ser. No. 09/370,541, filed Aug. 8, 1999, The 2'-position of the sugar moiety may be unsubstituted (i.e. 2'-deoxy), or substituted with a sugar substituent known in the art.

As used herein a sugar substituent is a substituent that is covalently attached to a position of the sugar moiety. Oligomeric compounds of the present invention may incorporate sugar moieties modified with sugar substituents to enhance one or more properties such as for example nuclease resistance or binding affinity. The 2'-position has been a preferred position for covalent attachment of sugar substituents. However, the 3' and 5' positions and the heterocyclic base moiety of selected nucleosides have also been modified with sugar substituents.

A representative list of sugar substituents useful in the present invention includes H (i.e. deoxy), —OH, alkyl, alkenyl, alkynyl, aryl, alkoxy, substituted alkoxy, alkenyloxy, substituted alkenyloxy, alkynyloxy, substituted alkynyloxy, aminoalkoxy, alkoxyalkoxy, alkylaminoalkoxy, imidazolylalkoxy, alkenylthio, alkynylthio, alkenylamino, alkynylamino, aryloxy, arylthio, aralkyloxy, aralkylthio, aralkylamino, N-phthalimido, halogen (e.g. fluoro), —C(=O)—R (wherein R is an organic radical), carboxyl, nitro, nitroso, cyano, trifluoromethyl, trifluoromethoxy, imidazolyl, azido, hydrazino, aminooxy, isocyanato, isothiocyanato, sulfoxide (—S(=O)—R), sulfone (—S(=O)$_2$—R (wherein R is an organic radical)), disulfide (—S—S—R (wherein R is an organic radical)), silyl, a heterocycle, a carbocycle, an intercalator, a reporter group, conjugate, polyamine, polyamide, polyalkylene glycol, and polyethers of the formula (O-alkyl)$_m$, where m is 1 to about 10. As used herein "sugar substituent" includes modifications (such as replacement of a hydroxyl with a hydrogen, i.e. deoxy modification), as well as modifications on the sugar hydroxy (wherein the H of the hydroxyl group is replaced by a substituent other than H), and modifications in which the sugar hydroxyl group is replaced with a group in which oxygen is not bonded to the sugar ring (see e.g. SH, NH$_2$, etc. herein). Suitable sugar modifications are described more fully herein.

Some preferred sugar modifications include hydrogen (e.g. 2'-deoxy), a hydroxyl protected by a protecting group, hydroxyl in which the H of the OH group has been replaced by substituted or unsubstituted alkyl, alkenyl or alkynyl (wherein the substituent groups are selected from hydroxyl, amino, alkoxy, carboxyl, benzyl, phenyl, nitro, thiol, thioalkoxy, halogen, alkyl, aryl, alkenyl and alkynyl). Further representative substituent groups are disclosed in U.S. Pat. No. 5,212,295, at column 12, lines 41–50, hereby incorporated by reference in its entirety.

Additional sugar modifications amenable to the present invention include those in which the 2'-hydroxyl group has been replaced by 2'-SR or 2'-N(R)$_2$. Some 2'-SR nucleosides are disclosed in U.S. Pat. No. 5,670,633, issued Sep. 23, 1997, hereby incorporated by reference in its entirety. The incorporation of 2'-SR monomer synthons are disclosed by Hamm et al., J. Org. Chem., 1997, 62, 3415–3420. 2'-N(R)$_2$ nucleosides are disclosed by Goettingen, M., J. Org. Chem., 1996, 61, 6273–6281; and Polushin et al., Tetrahedron Lett., 1996, 37, 3227–3230.

Preferred polyethers are linear and cyclic polyethylene glycols (PEGs), and (PEG)-containing groups, such as crown ethers and those which are disclosed by Ouchi et al. (Drug Design and Discovery 1992, 9, 93), Ravasio et al. (J. Org. Chem. 1991, 56, 4329) and Delgardo et. al. (Critical Reviews in Therapeutic Drug Carrier Systems 1992, 9, 249), each of which is herein incorporated by reference in its entirety. Further sugar modifications are disclosed in Cook, P. D., Anti-Cancer Drug Design, 1991, 6, 585–607. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, hereby incorporated by reference in its entirety.

Further representative substituent groups include groups of formula IX or X:

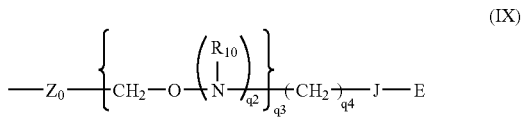

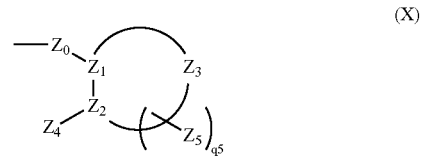

wherein:
Z$_0$ is O, S or NH;
J is a single bond, O or C(=O);
E is C$_1$–C$_{10}$ alkyl, N(R$_5$)(R$_6$), N(R$_5$)(R$_7$), N=C(R$_{5a}$)(R$_{6a}$), N=C(R$_{5a}$)(R$_{7a}$) or has formula:

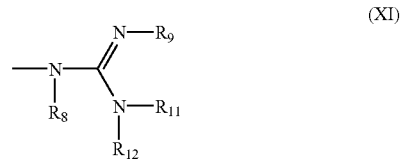

each R$_7$, R$_8$, R$_9$, R$_{11}$ and R$_{12}$ is, independently, hydrogen, C(O)R$_{13}$, substituted or unsubstituted C$_1$–C$_{10}$ alkyl, substituted or unsubstituted C$_2$–C$_{10}$ alkenyl, substituted or unsubstituted C$_2$–C$_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, R$_{11}$ and R$_{12}$, together form a phthalimido moiety with the nitrogen atom to which they are attached;

each R$_{13}$ is, independently, substituted or unsubstituted C$_1$–C$_{10}$ alkyl, trifluoromethyl, cyanoethyloxy, methoxy, ethoxy, t-butoxy, allyloxy, 9-fluorenylmethoxy, 2-(trimethylsilyl)-ethoxy,2,2,2-trichloroethoxy, benzyloxy, butyryl, iso-butyryl, phenyl or aryl;

$R_{10}$ is T—L,

T is a bond or a linking moiety;

L is a chemical functional group, a conjugate group or a solid support material;

each $R_5$ and $R_6$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl and alkynyl. Further representative alkyl substituents are disclosed in U.S. Pat. No. 5,212,295, at column 12, lines 41–50, hereby incorporated by reference in its entirety.

or $R_5$ and $R_6$, together, are a nitrogen protecting group or are joined in a ring structure that optionally includes an additional heteroatom selected from N and O or a chemical functional group;

each $R_{5a}$ and $R_{6a}$ is, independently, H, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl and alkynyl. Further representative alkyl substituents are disclosed in U.S. Pat. No. 5,212,295, at column 12, lines 41–50, hereby incorporated by reference in its entirety.

$R_{7a}$ is —T—L;

$Z_4$ is OM, SM, or $N(M)_2$;

each M is, independently, H, $C_1$–$C_8$ alkyl, $C_1$–$C_8$ haloalkyl, $C(=NH)N(H)R_{16}$, $C(=O)N(H)R_{16}$ or $OC(=O)N(H)R_{16}$;

$R_{16}$ is H or $C_1$–$C_8$ alkyl;

$Z_1$, $Z_2$ and $Z_3$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_5)(R_6)$ $OR_5$, halo, $SR_5$ or CN;

each $q_2$ is, independently, 0 or 1;

$q_3$ is 0 or an integer from 1 to 10;

$q_4$ is an integer from 1 to 10;

$q_5$ is from 0, 1 or 2; and provided that when $q_3$ is 0, $q_4$ is greater than 1.

Representative substituents of Formula IX are disclosed in U.S. Pat. No. 6,172,209, hereby incorporated by reference in its entirety.

Representative cyclic substituent groups of Formula X are disclosed in U.S. Pat. No. 6,271,358, hereby incorporated by reference in its entirety.

Particularly preferred sugar substituent groups include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10.

Some preferred oligomeric compounds of the invention contain, at least one nucleoside having one of the following substituent groups: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligomeric compound, or a group for improving the pharmacodynamic properties of an oligomeric compound, and other substituents having similar properties. A preferred modification includes 2'-methoxyethoxy [2'-O—$CH_2CH_2OCH_3$, also known as 2'-O-(2-methoxyethyl) or 2'-MOE] (Martin et al., Helv. Chim. Acta, 1995, 78, 486), i.e., an alkoxyalkoxy group. A further preferred modification is 2'-dimethylaminooxyethoxy, i.e., a $O(CH_2)_2ON(CH_3)_2$ group, also known as 2'-DMAOE. Representative aminooxy substituent groups are described in co-owned U.S. patent application Ser. No. 09/344,260, filed Jun. 25, 1999, entitled "Aminooxy-Functionalized Oligomers"; and U.S. patent application Ser. No. 09/370,541, filed Aug. 9, 1999, entitled "Aminooxy-Functionalized Oligomers and Methods for Making Same;" hereby incorporated by reference in their entirety.

Other preferred modifications include 2'-deoxy-2'-methoxy (i.e. the 2'-OH is replaced with a 2'-O—$CH_3$), 2'-deoxy-2'-aminopropoxy (2'-$OCH_2CH_2CH_2NH_2$) and 2'-deoxy-2'-fluoro (2'-F). Similar modifications may also be made at other positions on nucleosides and oligomers, particularly the 3' position of the sugar on the 3' terminal nucleoside or at a 3'-position of a nucleoside that has a linkage from the 2'-position such as a 2'-5' linked oligomer and at the 5' position of a 5' terminal nucleoside. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, also herein incorporated by reference.

Representative guanidino substituent groups that are shown in formula XI are disclosed in co-owned U.S. patent application Ser. No. 09/349,040, entitled "Functionalized Oligomers", filed Jul. 7, 1999, hereby incorporated by reference in its entirety.

Representative acetamido substituent groups are disclosed in U.S. Pat. No. 6,147,200, hereby incorporated by reference in its entirety.

Representative dimethylaminoethyloxyethyl substituent groups are disclosed in U.S. Pat. No. 6,043,352 and in International Patent Application PCT/US99/17895, entitled "2'-O-Dimethylaminoethyloxyethyl-Modified Oligonucleotides", filed Aug. 6, 1999, hereby incorporated by reference in their entirety.

In some embodiments of the present invention, the 2'-substituent 2'-OH, 2'-SH, 2'-aminoalkyloxyalkoxy (see U.S. Pat. No. 6,127,533 and U.S. Ser. No. 09/370,625, filed Aug. 6, 1999 each incorporated herein by reference in its entirety), 2'-aminooxy substituents (see U.S. Ser. No.

09/370,541, filed Aug. 9, 1999, incorporated herein by reference in its entirety), aminooxy substituents (see U.S. Ser. No. 09/344,260, filed Jun. 25, 1999,

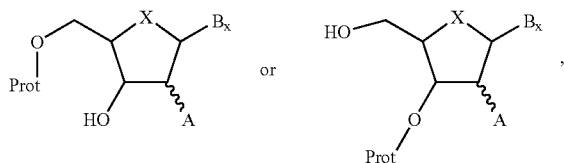

wherein $B_x$ is a nucleobase (as described herein), X is O, S, $CH_2$, $CHR_{10}$, $CR_{10}R_{11}$, NH or $NR_{10}$, $R_{10}$ and $R_{11}$ are independently selected from optionally substituted $C_1$–$C_{10}$ alkyl (straight-chain or branched), $C_2$–$C_{10}$ alkenyl (straight-chain or branched), $C_2$–$C_{10}$ alkynyl (straight-chain or branched), $C_1$–$C_{12}$ aryl, $C_1$–$C_{10}$ alkanoyl (optionally unsaturated in the hydrocarbyl portion of the alkanoyl group), or alkylsulfonyl (optionally unsaturated in the hydrocarbyl portion of the alkylsulfonyl group).

In particular embodiments of the present invention, $Q_1$ is a monomer such as:

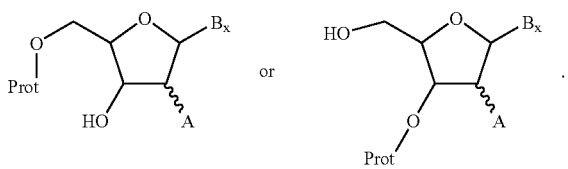

wherein Prot is a hydroxyl protecting group, A is a sugar substituent, and $B_x$ is a nucleobase, each as described more fully herein.

Other methods of making phosphoramidite are illustrated, for example, by Köster et al. in U.S. RE 34,069, which is specifically incorporated herein by reference.

Although a particular contemplated use of the purified phosphorodiamidites of the present invention is coupling of a mononucleotide to an active hydroxyl group of a nucleic acid sugar, a purified phosphorodiamidite will generally react with an active hydroxyl group of a broad range of compounds, including glycols, steroids, amino acids, peptides, etc. In this regard, the person skilled in the art will recognize that a phosphorodiamidite of the present invention may react with a compound $Q_1$-OH, incorporated herein by reference in its entirety), a substituent —$X_1$—$Y_1$, wherein $X_1$ is O, S, NR, $CR_2$ (R is alkyl) and $Y_1$ is substituted or unsubstituted alkyl, alkenyl, aryl (substituents are OH, $NH_2$, SH, COOH, amido, ester, aminoalkylamido, Si(alkyl)$_3$ or a drug moiety (see U.S. Pat. Nos. 5,466,786 and 5,792,847, each incorporated by reference in its entirety), 2-O—$X_2$, wherein $X_2$ is substituted alkyl, and the substituent is O-alkyl, S-alkyl, NH-alkyl, N-dialkyl, O-aryl, S-aryl, NH-aralkyl, O-aralkyl, S-aralkyl or NH-aralkyl (See U.S. Pat. No. 5,914,396, incorporated herein in its entirety), 2'-F (see U.S. Pat. No. 5,955,589, incorporated herein in its entirety), 2'-alkylsulfonyl, 2'-alkylsulfinyl (see U.S. Pat. No. 5,859,221, incorporated herein in its entirety), 2'-aminoalkyloxy or 2'-imidazolylalkyloxy (see U.S. Pat. No. 5,872,232, incorporated herein in its entirety), bromo, chloro, iodo, azido, amino, substituted amino, bromomethyl, chloromethyl, iodomethyl, cyanato, bromoalkoxy, chloroalkoxyl, iodalkoxyl, alkyl sulfide, alkyl sulfonate, nitrate or nitrite per Cook et al., U.S. Pat. No. 6,307,040, incorporated herein by reference, 2'-O-alkyl or 2'-fluoro per Bennett et al., U.S. Pat. No. 5,703,054, 2'-allyl or azido as taught by U.S. Ser. No. 09/389,283, filed Sep. 2, 1999, 2'-carbamates and 2'-amides as taught by U.S. Pat. No. 6,322,987, 2'-aminocarbonylalkoxy per U.S. Pat. No. 6,147,200, each of the foregoing patents and patent applications being expressly incorporated herein in their entireties.

In some embodiments of the present invention, A may be in a configuration other than the ribo-configuration (i.e. A bound to sugar ring by a down-bond). Such configurations include the arabino-configuration (A bound to the sugar ring by an up-bond).

Phosphorodiamidite can also be used in the synthesis of phosphorus functionalized sugars other than ribofuranoses. In some embodiments of the present invention, ribofuranosyl ring may be replaced by, inter alia, an erythrofuranosyl ring as taught by Cook et al. (U.S. Pat. Nos. 6,146,829 or 6,326,199).

Phosphorodiamidite can also be used in the synthesis of other phosphorus functionalized groups, such as phosphorus functionalized corticosteroids, estrogens, androgens, peptides, etc.

Once an oligonucleotide has been made using a purified phosphoramidite made by a process including a phosphorodiamidite purification process of the present invention, it is advantageously deprotected (if the process is carried out in solution phase) or cleaved from the solid support (if the process is carried out on a solid support). In either case, oligonucleotides made with purified phosphorodiamidite of the present invention may be used in numerous applications.

The present invention produces purified phosphorodiamidite that is useful in the synthesis of oligonucleotides. Such oligonucleotides are useful in various applications. For example some oligonucleotides are antisense compounds, which specifically hybridize with one or more nucleic acids encoding a target protein, such as a hematopoietic cell protein tyrosine kinase. As used herein, the terms "target nucleic acid" encompasses DNA whose expression is modulated by the oligonucleotide of interest, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of a target protein, such as a hematopoietic cell protein tyrosine kinase. In general, "modulation" means either an increase (stimulation) or a decrease (inhibition) in the expression of a gene.

It is preferred to target specific nucleic acids for antisense. "Targeting" an antisense compound to a particular nucleic acid, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. The targeting process also includes determination of a site or sites within this gene for the antisense interaction to occur such that the desired effect, e.g., detection or modulation of expression of the protein, will result. For example, in some contexts, an intragenic site may be the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In some contexts, "start codon" and "translation initiation codon" may refer to the codon or codons that are used in vivo to initiate translation of an mRNA molecule transcribed from a gene encoding hematopoietic cell protein tyrosine kinase, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can be effective, and therefore preferred, target regions for antisense compounds targeted, for example, to DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic regions.

Upon excision of one or more exon or intron regions or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, oligonucleotides are chosen which are sufficiently complementary to the target, i.e., hybridize sufficiently well and with sufficient specificity, to give the desired effect. In some contexts "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of activity, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation. The target sites to which these preferred sequences are complementary are generally referred to as "active sites" and are therefore preferred sites for targeting.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds made by processes of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis)(Sutcliffe, et al., *Proc. Natl. Acad. Sci. U.S.A.*, 2000, 97, 1976–81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF)(Fuchs, et al., *Anal. Biochem.*, 2000, 286, 91–98; Larson, et al., *Cytometry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (reviewed in (To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. In some cases, oligonucleotides made by process of the present invention can be 8 to about 50 nucleobases (i.e. from about 8 to about 50 linked nucleosides). Particularly preferred oligonucleotides antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds that may be made by processes of the present invention include oligonucleotides containing two or more moieties linked by a modified backbone, or non-natural internucleoside, linkage. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleotides. While the processes according to the present invention are directed toward making phosphorus-containing internucleoside linkages, it is to be understood that mixed-backbone structures are also achievable using phosphorodiamidite produced by processes according to the present invention. Such mixed-backbone structures, or hybrids, will contain one or more phosphorus-containing internucleoside linkage, and one or more non-phosphorus-containing internucleoside linkage. The person skilled in the art should recognize that where non-phosphorus backbones are referred to herein, such reference is to hybrids containing at least one internucleoside linkage formed using a phosphorodiamidite produced by processes of the present invention.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497–1500.

It is possible for two or more of the backbone nucleoside monomers to be joined to one another by with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S—or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE)(Martin et al., *Helv. Chim. Acta*, 1995, 78, 486–504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$, also described in examples hereinbelow.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methylene (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyl-adenine, 5-propynyluracil and 5-propynylcytosine. Also, 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds made in part by processes of the present invention may be formed as composite structures of two or more oligonucleotides, modified oligonucleotides, oligonucleotides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

Further down-stream processing of oligonucleotides made using processes of the present invention may include admixing, encapsulating, conjugating or otherwise associating the oligonucleotides with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Oligonucleotide compounds made by processes of the present invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives of the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotide compounds made by processes of the present invention can be utilized for diagnostics, therapeutics, prophylaxis and as research reagents and kits. For therapeutics, an animal, preferably a human, suspected of having a disease or disorder which can be treated by modulating the expression of hematopoietic cell protein tyrosine kinase is treated by administering antisense compounds in accordance with this invention. The compounds made by processes of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The oligonucleotide compounds made by processes of the present invention are useful for research and diagnostics, because these compounds hybridize to nucleic acids encoding specific proteins, such as hematopoietic cell protein tyrosine kinase, enabling sandwich and other assays to easily be constructed to exploit this fact. Hybridization of the oligonucleotide compounds made by processes of the present invention with a nucleic acid encoding a protein, such as hematopoietic cell protein tyrosine kinase, can be detected by means known in the art. Such means may include conjugation of an enzyme to the oligonucleotide, radiolabelling of the oligonucleotide or any other suitable detection means. Kits using such detection means for detecting the level of hematopoietic cell protein tyrosine kinase in a sample may also be prepared.

The oligonucleotides made by processes of the present invention may be used in pharmaceutical compositions and formulations which include the oligonucleotide compounds made by processes of the present invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearoylphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions comprising oligonucleotide compounds made by processes of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations comprising oligonucleotide compounds made by processes of the present invention, which may conveniently be presented in unit dosage form, may be prepared by conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The oligonucleotide compounds made by processes of the present invention may be formulated into any of many possible dosage forms such as, but not limited to, tablets, capsules, gel capsules, liquid syrups, soft gels, suppositories, and enemas. The oligonucleotide compounds made by processes of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In some embodiments of the present invention pharmaceutical compositions comprising oligonucleotide compounds made by processes of the present invention may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Compositions comprising the oligonucleotide compounds made by processes of the present invention may be prepared and formulated as emulsions. Emulsions are typically heterogeneous systems of one liquid dispersed in another in the form of droplets usually exceeding 0.1 μm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245;

Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In some embodiments of the present invention, the compositions comprising oligonucleotide compounds made by processes of the present invention may be formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (CA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the oligonucleotides prepared according to the present invention may also contain additional components and additives such as sorbitan monostearate (Grill 3), Labrasol, and penetration enhancers to improve the properties of the formulation and to enhance the absorption of the oligonucleotides made by processes according to the present invention. Penetration enhancers used in the microemulsions may be classified as belonging to one of five broad categories-surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used herein, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include: liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes that interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes that are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$ or (B) is derivatized with one or more hydrophilic polymers, such as a polyethylene glycol (PEG) moiety. While not wishing to be bound by any particular theory, it is thought that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765). Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

In some embodiments, the present invention may employ various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p. 92). Each of the above mentioned classes of penetration enhancers are described below in greater detail.

In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p. 92); and perfluorochemical emulsions, such as FC-43. Takahashi et al., *J. Pharm. Pharmacol.*, 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p. 92; Muranishi, *Critical Reviews in Therapeutic Drug Carrier Systems*, 1990, 7, 1–33; El Hariri et al., J. Pharm. Pharmacol., 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 *In: Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel.*, 1990, 14, 43–51).

As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrroles such as 2-pyrrol, azones, and terpenes such as limonene and menthone.

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulfate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Compositions comprising oligonucleotides made by processes of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Oligonucleotide compounds made by processes of the present invention may be formulated as pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

Compositions comprising oligonucleotides made by processes of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

The present invention will now be illustrated by reference to the following, non-limiting and illustrative examples.

EXAMPLE 1

2-Cyanoethyl tetraisopropylphosphorodiamidite
(Starting with Reagent Contaminated with 0-3% Ethylene Hexamethydisilazane (HMDS, 828 g, 5.13 mol) was added to the solution of 3-hydroxypropionitrile (710 g, 10 mol) and toluenesulfonic acid (1.0 g) at 100° C. over 0.5 h. The mixture was stirred at the same temperature for 2 h and distilled under reduced pressure. Bis-trimethylsilyl ethylene glycol is collected first at approximately 65° C. and 20 mmHg (~60 ml). the product (3-trimethylsilanyloxypropionitrile, or "silyl ether") was collected at 84–87° C. and 20 mmHg as a colorless liquid (1288.3 g).

The silyl ether was added to phosphorus trichloride (1624 g, 11.8 mol) with stirring at room temperature over 30 min. The reaction solution was stirred for 12 h at room temperature and evaporated under reduced pressure below 45° C. The residue was co-evaporated with hexanes (2×2 L) under the same conditions to give crude dichlorophosphite ($Cl_2PO$—$CH_2CH_2CN$) as a colorless liquid (1505 g).

A mixture of diisopropylamine (4.0 kg, 39.5 mol), hexanes (2 L) and anhydrous potassium carbonate (200 g) was stirred at −15° C. for 20 min. The crude dichlorophosphite was added to the diisopropylamine mixture while maintaining the reaction temperature below 0° C. The reaction mixture was stirred at 0° C. for 2 h and then allowed to warm to room temperature overnight and then poured into hexanes (18 L). The mixture was washed with water (4 L) and acetonitrile-water (60:40, v/v, 4×2 L). The hexane layer was evaporated and dried under vacuum (25° C. at 0.1 mmHg for 2 h) to give the desired product as a colorless, clear liquid (1870.5 g, total yield: 62%).

EXAMPLE 2

2-Cyanoethyl tetraisopropylphosphorodiamidite
(Starting with Pure Reagent)

HMDS (424 g, 2.6 mol) was added to a solution of 3-hydroxypropionitrile (355 g, 5.0 mol) and toluene sulfonic acid (TsOH, 0.5 g) at 60° C. over 0.5 h. The mixture was stirred at the same temperature for 2 h and evaporated at below 60° C. under reduced pressure to give crude 3-trimethylsilanyloxypropionitrile as a cloudy liquid (735 g).

The crude 3-trimethylsilanyloxypropionitrile was added to phosphorus trichloride (893 g, 6.5 mol) with stirring at room temperature over 30 min. The reaction solution was stirred for 12 h at room temperature and evaporated under reduced pressure below 45° C. The residue was co-evaporated with hexanes (2×1 L) under the same conditions to give crude dichlorophosphite (807 g).

A mixture of diisopropylamine, hexane and anhydrous potassium carbonate was stirred at −15° C. for 20 min. The crude dichlorophosphite was added at a temperature below −5° C. for 20 min. The reaction mixture was stirred at 0° C. for 2 h, then allowed to warm to room temperature overnight, and then poured into hexanes (5 L). The mixture was washed (2 L) with water and acetonitrile-water (60:40, v/v, 4×1 L). The hexane layer was evaporated to give the desired product as a clear, colorless liquid (1080 g, yield: 72%).

EXAMPLE 3

2-Cyanoethyl tetraisopropylphosphorodiamidite

3-Trimethylsilanyloxypropionitrile (7.56 kg, 52.8 mol) was added to phosphorus trichloride (6 L, (~9.4 Kg), 68.8 mol) with stirring at room temperature over 30 min. The reaction solution was stirred for 12 h at room temperature and evaporated under reduced pressure below 45° C. The residue was co-evaporated with cyclohexane (2×2 L) under the same conditions to give crude diclorophosphite as a yellow liquid (9.6 kg).

Diisopropylamine (1 L, 7.12 mol), hexane (1 L) were cooled to 0° C. Phosphorus oxychloride (4.5 ml) was added and the mixture was stirred for 20 min. The crude dichlorophosphite (258 g, 1.5 mol) was added with temperature below 0° C. over 1 hour. The reaction mixture was stirred at room temperature overnight and poured into hexane (1 L).

The mixture was washed with water (1 L) and acetonitrile-water (70:30, v/v, 4×500 ml). The hexane layer was evaporated to give the desired product as a colorless liquid (239 g).

EXAMPLE 4

2-Cyanoethyl tetraisopropylphosphorodiamidite

HMDS (15.5 L, 73.5 mol) was added to a solution of 3-hydroxypropionitrile (10 kg, 141 mol) and toluenesulfonic acid (10.0 g) at 60–80° C. over 1 hour. The mixture was stirred at 80° C. for 3.5 h. The early fraction (4 L) of distillation from a previous batch was added and the mixture was distilled under reduced pressure (20 mmHg). The first two liters were discarded and the next four liters were collected for recycle in next run. The product, 3-trimethylsilanyloxypropionitrile (22 L), was collected until a volume of 0.5 L was left in the distillation vessel.

The 3-trimethylsilanyloxypropionitrile (1290 g, 9 mol) was added to phosphorus trichloride (1 L, 11.7 mol) with stirring at room temperature over 30 min. The reaction solution was stirred for 12 h at room temperature and evaporated under reduced pressure below 40° C. The residue was co-evaporated with hexanes (1 L) under the same conditions to give the dichlorophosphite as a colorless liquid (1430 g).

Phosphorus oxychloride (25 ml) was added to the solution of diisopropylamine (5.5 L, 39.2 mol) and hexanes (4 L) at 0° C. and the mixture was stirred for 20 min. The above crude dichlorophosphite was added while maintaining the reaction temperature below 10° C. over 1 hour. The reaction mixture was then allowed to warm to room temperature and stirred for 5 h. The mixture was poured into hexanes (8 L). The mixture was washed with water (6 L), acetonitrile-0.1 N NaOH (70:30, v/v, 4×2 L) and acetonitrile-water (70:30, v/v, 2×2 L). The hexane layer was evaporated and dried under vacuum (25° C./0.5 mmHg/2 h) to give the desired product as a colorless, clear liquid (1.88 kg).

Summary

As discussed in the foregoing description of the invention, and as illustrated in the foregoing, non-limiting examples, the present invention provides a scalable process for purifying phosphorodiamidite. The present invention possesses the advantage that, unlike the previously-used distillation methods for purifying phosphorodiamidite, the present invention does not require subjecting the phosphorodiamidite product to elevated temperatures or pressures for extended periods of time. In fact, the present process may be conducted at or near room temperature and under atmospheric or near-atmospheric pressure. Thus, the present purification process does not tend to degrade the phosphorodiamidite product, which results in improved yield and purity of the purified phosphorodiamidite product of the present invention as compared to prior art processes.

Additionally, the purified phosphorodiamidite made by a process of the present has the advantage that it may be used to prepare higher-quality oligonucleotides than are possible with prior art purification processes. By efficiently eliminating impurities found in the crude phosphorodiamidite, and by avoiding the breakdown products associated with high temperature distillation, the inventive purification process produces an improved purified phosphorodiamidite reagent, which in turn achieves greater coupling efficiency, as well as improved purity of down-stream products, including oligonucleotides. Thus, the purification process of the present invention has impact on the entire process of oligonucleotide synthesis. Thus, the present invention makes it possible to prepare large quantities of oligonucleotide that are amenable to a variety of applications, including analytical, diagnostic and therapeutic uses.

All references cited herein are expressly incorporated herein in their entirety.

While the present invention has been described with specificity in accordance with certain of its preferred embodiments, the foregoing examples serve only to illustrate the invention and are not intended to limit the same. One having skill in the art will appreciate that other embodiments are possible within the scope of the present invention.

We claim:

1. A process of producing a purified phosphorodiamidite, said process comprising the steps of:
   a. dissolving a crude phosphorodiamidite containing at least one impurity in an apolar phase; and
   b. contacting the apolar phase with a polar phase comprising a polar organic solvent, whereby at least a portion of the impurity is transferred into the polar phase and the purified phosphorodiamidite is produced in the apolar phase;

wherein said phosphorodiamidite is represented by formula I:

$G_1$ is $OR_1$;
$R_1$ is cyanoethyl;
each $G_2$ is independently $-NR_2R_3$, and
$R_2$ and $R_3$ are independently alkyl, substituted alkyl, alkenyl, substituted alkenyl.

2. The process of claim 1, wherein the phosphorodiamidite is the most lipophilic solute in the apolar phase of step (a).

3. The process of claim 1, wherein the apolar phase comprises a liquid hydrocarbon.

4. The process of claim 3, wherein the apolar phase comprises alkanes.

5. The process of claim 1, wherein the polar phase comprises acetonitrile, N,N-dimethylformamide (DMF), ethylene glycol, glycerol, acetamide, ethylene diamine, N,N,-dimethylacetamide, N-methylacetamide, N-methylformamide, dimethylsulfoxide, ethanolamine, diethanolamine, triethanolamine, caprolactam, 3-hydroxypropiononitrile, hexamethylphosphoric triamide, dimethylurea, tetramethylurea, 2-pyrrolidinone, N-methylpyrrolidinone or 2-imidazolidone.

6. The process of claim 5, wherein the apolar phase comprises hexanes.

7. The process of claim 6, wherein the polar phase comprises acetonitrile.

8. The process of claim 7, wherein the polar phase further comprises water.

9. The process of claim 8, wherein the polar phase comprises a mixture of acetonitrile and water in the range of about 50:50 to about 90:5 (v/v).

10. The process of claim 9, wherein the polar phase comprises a mixture of acetonitrile and water in the range of about 50:50 to about 80:20 (v/v).

11. The process of claim 3, wherein the apolar phase comprises toluene.

12. The process of claim 11, wherein the polar phase comprises acetonitrile, N,N-dimethylformamide (DMF), ethylene glycol, glycerol, acetamide, ethylene diamine, N,N,-dimethylacetamide, N-methylacetamide, N-methylformamide, dimethylsulfoxide, ethanolamine, diethanolamine, triethanolamine, caprolactam, 3-hydroxypropiononitrile, hexamethylphosphoric triamide, dimethylurea, tetramethylurea, 2-pyrrolidinone, N-methylpyrrolidinone or 2-imidazolidone.

13. The process of claim 1, further comprising at least one additional step of contacting a polar phase with the apolar phase.

14. The process of claim 1, wherein the apolar phase and the polar phase are contacted at room temperature.

15. The process of claim 1, wherein the apolar phase and the polar phase are contacted with agitation.

16. The process of claim 1, further comprising the following step (c):
(c) separating the apolar phase from the polar phase.

17. The process of claim 1, further comprising the following steps (c) and (d):
(c) separating the apolar phase from the polar phase; and
(d) removing the apolar organic solvent from the purified phosphorodiamidite.

18. The process of claim 1, wherein the phosphorodiamidite is the most hydrophobic compound in the apolar phase.

19. A process of purifying a phosphorodiamidite compound of formula Va:

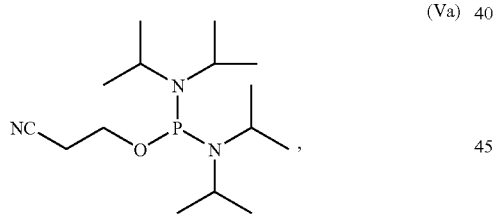

said process comprising the steps of:
a. dissolving the phosphorodiamidite of formula Va and at least one impurity in an apolar organic solvent to form an apolar phase; and
b. contacting the apolar phase with a polar phase comprising a polar organic solvent, whereby at least a portion of the impurity partitions into the polar phase, thereby producing the purified phosphorodiamidite in the apolar phase.

20. The process of claim 19, wherein the apolar phase comprises hexanes.

21. The process of claim 19, wherein the polar phase comprises acetonitrile.

22. The process of claim 21, wherein the polar phase further comprises water.

23. The process of claim 22, wherein the polar phase comprises acetonitrile and water in a ratio within the range of about 50:50 to about 95:5 (v/v).

24. The process of claim 23, wherein the polar phase comprises acetonitrile and water in a ratio within the range of about 50:50 to about 80:20 (v/v).

25. The process of claim 19, wherein the process is carried out at about room temperature.

26. The process of claim 19, further comprising at least one additional step of contacting a polar phase with the apolar phase.

27. The process of claim 19, wherein the apolar phase and the polar phase are contacted at room temperature.

28. The process of claim 19, wherein the apolar phase and the polar phase are contacted with agitation.

29. The process of claim 19, further comprising the following step c.:
c. separating the apolar phase from the polar phase.

30. The process of claim 19, further comprising the following steps c. and d.:
c. separating the apolar phase from the polar phase; and
d. removing the apolar organic solvent from the purified phosphorodiamidite.

31. The process of claim 19, wherein the phosphorodiamidite of formula Va is the most lipophilic compound in the apolar phase of step a.

32. The process of claim 19, wherein the phosphorodiamidite is the most lipophilic compound in the apolar phase of step a.

33. A process of making a purified phosphorodiamidite, said process comprising
a. obtaining a crude phosphorodiamidite composition comprising phosphorodiamidite and at least one impurity;
b. dissolving said crude phosphorodiamidite composition in an apolar organic solvent to form an apolar phase;
c. contacting said apolar phase with a polar phase comprising a polar organic solvent, whereby at least a portion of said impurity partitions into the polar phase; and
d. separating the apolar phase from the polar phase, whereby a purified phosphorodiamidite is obtained in the apolar phase wherein said phosphorodiamidite is represented by formula I:

$G_1$ is $OR_1$;
$R_1$ is cyanoethyl;
each $G_2$ is independently —$NR_2R_3$, and
$R_2$ and $R_3$ are independently alkyl, substituted alkyl, alkenyl, substituted alkenyl.

34. The process of claim 1, wherein said apolar phase is hexane and said polar phase is a mixture of acetonitrile and water.

* * * * *